US00PP13542P2

(12) United States Plant Patent
Hirabayashi

(10) Patent No.: US PP13,542 P2
(45) Date of Patent: Feb. 4, 2003

(54) PETUNIA PLANT NAMED 'KEILAVBU'

(75) Inventor: Hiroshi Hirabayashi, deceased, late of Yachiyo (JP), by Eriko Hirabayashi, Minako Hirabayashi, Kanako Hirabayashi, heirs

(73) Assignee: Jackson & Perkins Wholesale, Inc., Melford, OR (US)

( * ) Notice: Subject to any disclaimer, the term of this patent is extended or adjusted under 35 U.S.C. 154(b) by 0 days.

(21) Appl. No.: 09/747,813

(22) Filed: Dec. 22, 2000

(51) Int. Cl.[7] ..... A01H 5/00
(52) U.S. Cl. ..... Plt./356
(58) Field of Search ..... Plt./356

(56) References Cited

PUBLICATIONS

UPOV–ROM Computer Database, 2001/06, GTI Jouve Retrieval Software, citation for 'Keilavbu'.*

* cited by examiner

*Primary Examiner*—Bruce R. Campell
*Assistant Examiner*—Susan B. McCormick
(74) *Attorney, Agent, or Firm*—Klarquist Sparkman, LLP

(57) ABSTRACT

Petunia plant having blue flowers; ease of propagation by cuttings; vigorous growth; trailing or spreading habit; and resistance to heat and rain.

1 Drawing Sheet

GENUS SPECIES

*Petunia×hybrida.*

VARIETY DENOMINATION

'KEIlavbu'.

SUMMARY OF THE INVENTION

The present invention relates to a new and distinct variety of petunia which was originated by me by crossing an unnamed seedling with an unnamed seedling.

BACKGROUND OF THE INVENTION

The primary objective of this breeding was to produce a new petunia variety having a trailing or spreading habit of growth, blue flowers, resistance to heat and rain, ease of propagation from cuttings and a profusion of flowering during the spring, summer and fall.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Blue flowers;
2. Ease of propagation by cuttings;
3. Vigorous growth;
4. Trailing or spreading habit; and
5. Resistance to heat and rain.

Asexual reproduction of this new variety by cuttings, as performed at Somis, Calif., shows that the foregoing and all other characteristics and distinctions come true to form and are established and transmitted through succeeding propagations.

COMPARISON WITH PARENTS

The variety 'KEIlavbu' is distinguishable from its parents in that neither possesses the pendent growth and bluish flowers of 'KEIlavbu'.

COMPARISON WITH SIMILAR VARIETY

Compared with Surfina Blue Vein, 'KEIlavbu' has a greater growth habit and a well-formed plant shape. As compared to other trailing petunias, 'KEIlavbu's' flower color is new and unique.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new petunia cultivar with color descriptions using terminology in accordance with The Royal Horticultural Society (London) Colour Chart (1966), except where ordinary dictionary significance of color is indicated.

Parentage:
*Seed parent.*—Unnamed seedling.
*Pollen parent.*—Unnamed seedling.

FLOWER

Observations made from specimens beginning at four months of age grown in a garden environment at Somis, Calif. in July, 1999–November, 2000.

Blooming habit: Blooms spring, summer and fall.

Plant:

*Growth*.—Decumbent.

*Growth habit*.—Vigorous, spreading.

*Rooting period*.—8–12 days at 72° F.

*Mature plant*.—Height: 11–15 cm. Spreading area: 110–150 cm in diameter.

*Blooming period*.—April to October.

*Stem*.—Overall Length: 50–80 cm. Main Stem: 20–25 cm. Laterals: 10–15 cm. Thickness: 2–3 mm. Color: Yellow-Green Group 144B–144C. Pubescence: Medium. Mode of Branching: Abundant. Length of Internode: 1–2 cm.

*Leaf*.—Arrangement on stem: Opposite. Shape: Elliptic. Margin: Entire. Size: Length: 5–6 cm. Width: 2.7–3.2 cm. Thickness: 0.3 mm. Color: Upper Surface: Green Group 137C to 137D. Lower Surface: Green Group 137C to 137D. Phyllotaxis: Opposite both before and after flowering. Texture: Pubescent. Venation pattern: Costate. Vein Color: Yellow-Green Group 146B. Petiole: Length: 3 to 11 mm. Diameter: 1 to 3 mm. Color: Yellow-Green Group 146B.

Flower:

*Orientation at opening*.—Faces slightly upward.

*Size*.—Average open diameter is about 5–6 cm.

*Type*.—Single.

*Shape*.—Corolla is thin with a length of 40–45 mm. Flower has a funnel shape with a five-fissured limb.

*Color*.—The upper sides of the petals vary from Violet Group 84A to 86D and Violet-Blue Group 91A. The petal also has variegation of Violet-Blue 92D and 97D with a pale throat of Green-Yellow Group 1D. The reverse sides of the petals are Green-Yellow Group 1D. The base of the petals has a small area of Green-Yellow Group 1D.

*Petal tip shape*.—Obverse.

*Lobation*.—Shallow.

*Waving*.—Weak.

*Peduncle*.—Length: 1.5–2.0 cm. Color: Yellow-Green Group 144B.

*Calyx*.—Number of sepals: 5. Length: 13–16 mm. Color: Upper surfaces: Yellow-Green Group 146B. Lower surface: Green Group 143C.

*Lastingness*.—Three days.

*Fragrance*.—Light vanilla.

Reproductive parts:

*Stamens*.—Quantity: Five normal stamens. Length: 11–13 mm.

*Anthers*.—Number: 5. Length: 1 mm. Color: Blue-Violet Group 94A.

*Filaments*.—Length: 10–12 mm. Color: Blue-Violet Group 92D.

*Pistil*.—Quantity: One normal pistil. Length: 10–12 mm.

*Stigma*.—Color: Green Group 137B. Length: 2 mm.

*Style*.—Color: Violet-Blue Group 92D. Length: 8–9 mm.

*Fruit*.—None observed.

Disease resistance: Resistant to mildew under normal growing conditions.

Response to climatic conditions: Excellent tolerance to heat and rain.

I claim:

1. A new and distinct variety of petunia plant, substantially as herein shown and described, characterized particularly by its blue flowers; ease of propagation by cuttings; vigorous growth; trailing or spreading habit; and resistance to heat and rain.

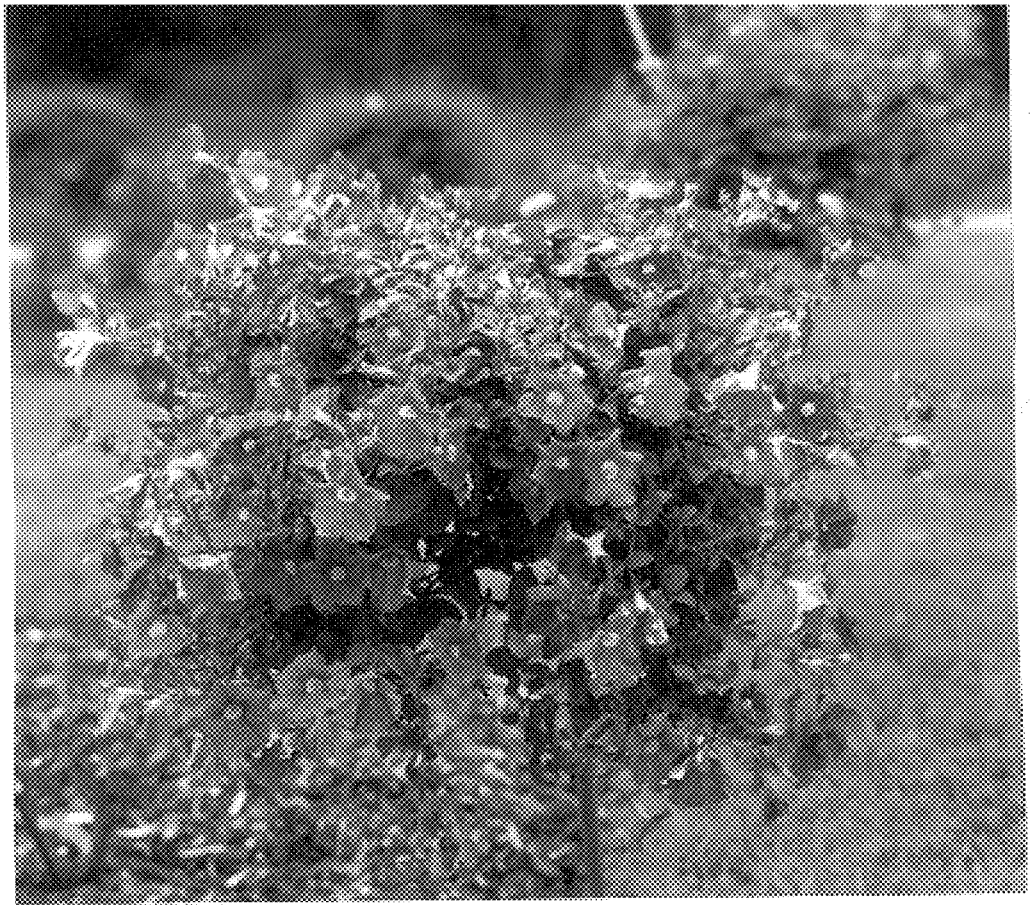

* * * * *